(12) United States Patent
Levine et al.

(10) Patent No.: US 10,517,630 B2
(45) Date of Patent: *Dec. 31, 2019

(54) ROTATIONAL THROMBECTOMY WIRE

(71) Applicant: Rex Medical, L.P., Conshohocken, PA (US)

(72) Inventors: Marc-Alan Levine, Pottstown, PA (US); Michael Leedle, Auduban, PA (US); John D. Leedle, Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 232 days.

This patent is subject to a terminal disclaimer.

(21) Appl. No.: 15/640,196

(22) Filed: Jun. 30, 2017

(65) Prior Publication Data

US 2017/0296220 A1    Oct. 19, 2017

Related U.S. Application Data

(60) Continuation of application No. 14/170,577, filed on Feb. 1, 2014, now Pat. No. 9,700,346, which is a
(Continued)

(51) Int. Cl.
*A61B 17/3207* (2006.01)
*A61B 17/32* (2006.01)
*A61B 17/00* (2006.01)

(52) U.S. Cl.
CPC ............... *A61B 17/320725* (2013.01); *A61B 17/320758* (2013.01); *A61B 17/32002* (2013.01);
(Continued)

(58) Field of Classification Search
CPC .............. A61B 17/32; A61B 17/32002; A61B 17/3207; A61B 17/320725; A61B 17/320758; A61B 2017/320024; A61B 2017/320032; A61B 2017/320733; A61B 2017/320766; A61B 2017/320775; A61B 2090/031

See application file for complete search history.

(56) References Cited

U.S. PATENT DOCUMENTS 3,612,058 A    10/1971    Ackerman
3,749,085 A    7/1973    Wilson et al.
(Continued)

FOREIGN PATENT DOCUMENTS

DE    1075903    2/1960
DE    3804849    9/1988
(Continued)

*Primary Examiner* — Ryan J. Severson
(74) *Attorney, Agent, or Firm* — Neil D. Gershon

(57) ABSTRACT

A rotational thrombectomy wire for breaking up vascular thrombus or other obstructive material having a core having a proximal portion and a distal portion. The distal portion has a smaller diameter than the proximal portion. A cable extends distally of the core. The cable has a first covering material positioned external thereof. A first coil is attached to a distal portion of the cable and has a diameter larger than a diameter of the cable and has a second covering material positioned thereover. The wire is rotatable by a motor.

18 Claims, 9 Drawing Sheets

Related U.S. Application Data division of application No. 13/095,329, filed on Apr. 27, 2011, now Pat. No. 8,663,259.

(60) Provisional application No. 61/334,412, filed on May 13, 2010.

(52) U.S. Cl.
CPC ............... *A61B 2017/00331* (2013.01); *A61B 2017/320733* (2013.01); *A61B 2017/320775* (2013.01)

(56) References Cited

U.S. PATENT DOCUMENTS

| | | | |
|---|---|---|---|
| 4,038,985 A | 8/1977 | Chiulli | |
| 4,579,127 A | 4/1986 | Haacke | |
| 4,651,856 A * | 3/1987 | Skrobisch | ............... F16D 7/025 192/150 |
| 4,745,919 A | 5/1988 | Bundy | |
| 4,765,332 A | 8/1988 | Fischell et al. | |
| 4,784,636 A | 11/1988 | Rydell | |
| 4,842,579 A | 6/1989 | Shiber | |
| 4,883,460 A | 11/1989 | Zanetti | |
| 4,895,560 A | 1/1990 | Papantonakos | |
| 4,906,244 A | 3/1990 | Pinchuk et al. | |
| 4,950,277 A | 8/1990 | Farr | |
| 4,957,482 A | 9/1990 | Shiber | |
| 4,979,951 A | 12/1990 | Simpson | |
| 4,984,581 A | 1/1991 | Stice et al. | |
| 4,990,134 A | 2/1991 | Auth | |
| 5,009,659 A | 4/1991 | Hamlin et al. | |
| 5,019,089 A | 5/1991 | Farr | |
| 5,025,799 A | 6/1991 | Wilson | |
| 5,026,384 A | 6/1991 | Farr et al. | |
| 5,030,201 A | 7/1991 | Palestrant | |
| 5,041,082 A | 8/1991 | Shiber | |
| 5,047,040 A | 9/1991 | Simpson | |
| 5,067,489 A | 11/1991 | Lind et al. | |
| 5,067,957 A | 11/1991 | Jervis | |
| 5,097,849 A | 3/1992 | Kensey | |
| 5,131,406 A | 7/1992 | Kaltenback | |
| 5,192,268 A | 3/1993 | Shiber | |
| 5,192,290 A | 3/1993 | Hilal | |
| 5,203,772 A | 4/1993 | Hammerslag et al. | |
| 5,211,183 A | 5/1993 | Wilson | |
| 5,213,111 A | 5/1993 | Cook | |
| 5,217,026 A | 6/1993 | Stoy | |
| 5,251,640 A | 10/1993 | Osborne | |
| 5,253,653 A | 10/1993 | Daigle | |
| 5,261,877 A | 11/1993 | Fine et al. | |
| 5,273,526 A | 12/1993 | Dance | |
| 5,287,858 A | 2/1994 | Hammerslag | |
| 5,299,580 A | 4/1994 | Atkinson | |
| 5,312,427 A | 5/1994 | Shturman | |
| 5,313,967 A | 5/1994 | Lieber | |
| 5,314,407 A | 5/1994 | Auth et al. | |
| 5,314,438 A | 5/1994 | Shturman | |
| 5,333,620 A | 8/1994 | Moutafis et al. | |
| 5,341,818 A | 8/1994 | Abrams | |
| 5,345,945 A | 9/1994 | Hodgson | |
| 5,356,418 A | 10/1994 | Shturman | |
| 5,372,144 A | 12/1994 | Martier | |
| 5,376,100 A | 12/1994 | Lefebvre | |
| 5,383,460 A | 1/1995 | Jang et al. | |
| 5,395,311 A | 3/1995 | Andrews | |
| 5,395,384 A | 3/1995 | Duthoit | |
| 5,429,136 A | 7/1995 | Milo et al. | |
| 5,431,673 A | 7/1995 | Summers et al. | |
| 5,452,726 A | 9/1995 | Burmeister | |
| 5,490,859 A | 2/1996 | Mische | |
| 5,501,694 A | 3/1996 | Ressemann et al. | |
| 5,514,128 A | 5/1996 | Hillsmon | |
| 5,529,580 A | 6/1996 | Kusunoki et al. | |
| 5,536,242 A | 7/1996 | Willard et al. | |
| 5,540,707 A | 7/1996 | Resseman et al. | |
| 5,551,443 A | 9/1996 | Sepetka | |
| 5,556,408 A | 9/1996 | Farhat | |
| 5,562,275 A | 10/1996 | Weissenfluh | |
| 5,569,179 A | 10/1996 | Adrian et al. | |
| 5,569,275 A | 10/1996 | Kotula et al. | |
| 5,584,843 A | 12/1996 | Wulfman | |
| 5,605,162 A | 2/1997 | Mirzaee | |
| 5,609,602 A | 3/1997 | Machemer et al. | |
| 5,611,807 A | 3/1997 | O'Boyle | |
| 5,634,897 A | 6/1997 | Dance | |
| 5,653,696 A | 8/1997 | Shiber | |
| 5,653,722 A | 8/1997 | Kieturakis | |
| 5,695,506 A | 12/1997 | Pike et al. | |
| 5,712,543 A | 1/1998 | Sjostrom | |
| 5,746,701 A | 5/1998 | Noone | |
| 5,749,885 A | 5/1998 | Sjostrom et al. | |
| 5,762,637 A | 6/1998 | Berg et al. | |
| 5,766,191 A | 6/1998 | Trerotola | |
| 5,797,856 A | 8/1998 | Frisbie et al. | |
| 5,833,631 A | 11/1998 | Nguyen | |
| 5,836,868 A | 11/1998 | Ressemann et al. | |
| 5,836,893 A | 11/1998 | Urick | |
| 5,840,046 A | 11/1998 | Deem | |
| 5,843,103 A | 12/1998 | Wulfman | |
| 5,879,361 A | 3/1999 | Nash | |
| 5,885,227 A | 3/1999 | Finlayson | |
| 5,895,399 A | 4/1999 | Barbut | |
| 5,897,567 A | 4/1999 | Ressemann et al. | |
| 5,902,263 A | 5/1999 | Patterson | |
| 5,902,268 A | 5/1999 | Saab | |
| 5,906,627 A | 5/1999 | Spaulding | |
| 5,910,364 A | 6/1999 | Miyata | |
| 5,916,166 A | 6/1999 | Reiss | |
| 5,924,998 A | 7/1999 | Cornelius | |
| 5,938,623 A | 8/1999 | Quiachon | |
| 5,938,645 A | 8/1999 | Gordon | |
| 5,957,941 A | 9/1999 | Ream | |
| 5,971,991 A | 10/1999 | Sunderland | |
| 5,984,877 A | 11/1999 | Fleischhacker, Jr. | |
| 6,004,279 A | 12/1999 | Crowley | |
| 6,007,533 A | 12/1999 | Casscells et al. | |
| 6,015,420 A | 1/2000 | Wulfman | |
| 6,019,736 A | 2/2000 | Avellanet | |
| 6,022,363 A | 2/2000 | Walker | |
| 6,024,749 A | 2/2000 | Shturman et al. | |
| 6,059,745 A | 5/2000 | Gelbfish | |
| 6,077,282 A | 6/2000 | Shturman et al. | |
| 6,080,117 A | 6/2000 | Cornelius | |
| 6,080,170 A | 6/2000 | Nash et al. | |
| 6,083,198 A | 7/2000 | Afzal | |
| 6,090,118 A | 7/2000 | McGuckin, Jr. | |
| 6,090,123 A | 7/2000 | Culp et al. | |
| 6,096,001 A | 8/2000 | Drasler et al. | |
| 6,106,485 A | 8/2000 | McMahan | |
| 6,113,614 A | 9/2000 | Mears | |
| 6,120,515 A | 9/2000 | Rogers et al. | |
| 6,126,635 A | 10/2000 | Simpson | |
| 6,143,009 A | 11/2000 | Shiber | |
| 6,165,140 A | 12/2000 | Ferrera et al. | |
| 6,168,570 B1 | 1/2001 | Ferrera et al. | |
| 6,183,487 B1 | 2/2001 | Barry | |
| 6,185,449 B1 | 2/2001 | Berg | |
| 6,206,898 B1 | 3/2001 | Honeycutt et al. | |
| 6,217,589 B1 | 4/2001 | McAlister | |
| 6,217,595 B1 | 4/2001 | Shturman | |
| 6,251,085 B1 | 6/2001 | Tezuka | |
| 6,251,086 B1 | 6/2001 | Cornelius | |
| 6,251,121 B1 | 6/2001 | Saadat | |
| 6,254,550 B1 | 7/2001 | McNamara | |
| 6,309,399 B1 | 10/2001 | Barbut et al. | |
| 6,319,242 B1 | 11/2001 | Patterson et al. | |
| 6,319,262 B1 | 11/2001 | Bates et al. | |
| 6,322,572 B1 | 11/2001 | Lee | |
| 6,328,752 B1 | 12/2001 | Sjostrom et al. | |
| 6,371,928 B1 | 4/2002 | McFann et al. | |
| 6,398,773 B1 | 6/2002 | Bagaoisan et al. | |
| 6,402,706 B2 | 6/2002 | Richardson | |
| 6,413,222 B1 | 7/2002 | Pantages et al. | |

(56) References Cited

U.S. PATENT DOCUMENTS

| | | |
|---|---|---|
| 6,432,066 B1 | 8/2002 | Ferrara et al. |
| 6,451,036 B1 | 9/2002 | Heitzmann et al. |
| 6,454,717 B1 | 9/2002 | Pantages et al. |
| 6,454,775 B1 | 9/2002 | Demarais et al. |
| 6,454,779 B1 | 9/2002 | Taylor |
| 6,458,127 B1 | 10/2002 | Truckai et al. |
| 6,475,222 B1 | 11/2002 | Berg et al. |
| 6,475,224 B1 | 11/2002 | Pantages et al. |
| 6,475,226 B1 | 11/2002 | Belef |
| 6,482,215 B1 | 11/2002 | Shiber |
| 6,482,217 B1 | 11/2002 | Pintor et al. |
| 6,485,482 B1 | 11/2002 | Belef |
| 6,491,660 B2 | 12/2002 | Guo et al. |
| 6,494,890 B1 | 12/2002 | Shturman |
| 6,508,782 B1 | 1/2003 | Evans |
| 6,508,825 B1 | 1/2003 | Selmon et al. |
| 6,517,528 B1 | 2/2003 | Pantages et al. |
| 6,517,560 B1 | 2/2003 | Toth et al. |
| 6,565,588 B1 | 5/2003 | Clement et al. |
| 6,569,147 B1 | 5/2003 | Evans et al. |
| 6,572,630 B1 | 6/2003 | McGuckin |
| 6,579,246 B2 | 6/2003 | Jacobson |
| 6,579,299 B2 | 6/2003 | McGuckin |
| 6,602,207 B1 | 8/2003 | Mam |
| 6,602,262 B2 | 8/2003 | Greigo et al. |
| 6,602,264 B1 * | 8/2003 | McGuckin, Jr. ....... A61B 17/22 606/159 |
| 6,620,114 B2 | 9/2003 | Urba |
| 6,620,179 B2 | 9/2003 | Boock |
| 6,632,230 B2 | 10/2003 | Barry |
| 6,648,337 B1 | 11/2003 | Baehl |
| 6,652,480 B1 | 11/2003 | Imran et al. |
| 6,652,546 B1 | 11/2003 | Nash |
| 6,660,014 B2 | 12/2003 | Demarais |
| 6,663,613 B1 | 12/2003 | Evans et al. |
| 6,666,874 B2 | 12/2003 | Heitzmann et al. |
| 6,669,652 B2 | 12/2003 | Anderson |
| 6,673,025 B1 | 1/2004 | Richardson |
| 6,685,718 B1 | 2/2004 | Wyzgala et al. |
| 6,689,089 B1 | 2/2004 | Tiedtke et al. |
| 6,702,830 B1 | 3/2004 | Demarais et al. |
| 6,719,717 B1 | 4/2004 | Johnson et al. |
| 6,746,462 B1 | 6/2004 | Selmon et al. |
| 6,758,818 B2 * | 7/2004 | Pantages ................. A61B 8/12 600/466 |
| 6,758,851 B2 | 7/2004 | Shiber |
| 6,767,353 B1 | 7/2004 | Shiber |
| 6,790,215 B2 | 9/2004 | Findlay |
| 6,805,676 B2 | 10/2004 | Klint |
| 6,805,684 B2 | 10/2004 | Bonnette et al. |
| 6,818,001 B2 * | 11/2004 | Wulfman ....... A61B 17/320758 606/159 |
| 6,824,545 B2 * | 11/2004 | Sepetka ........... A61B 17/22031 606/113 |
| 6,830,577 B2 | 12/2004 | Nash et al. |
| 6,881,194 B2 | 4/2005 | Miyata et al. |
| 6,911,016 B2 | 6/2005 | Balzum et al. |
| 6,926,725 B2 * | 8/2005 | Cooke ............ A61B 17/320758 606/159 |
| 6,929,633 B2 | 8/2005 | Evans et al. |
| 7,037,316 B2 * | 5/2006 | McGuckin, Jr. ....... A61B 17/22 606/113 |
| 7,074,197 B2 | 7/2006 | Reynolds et al. |
| 7,115,101 B2 | 10/2006 | Cornelius et al. |
| 7,150,756 B2 | 12/2006 | Levinson et al. |
| 7,169,118 B2 | 1/2007 | Reynolds |
| 7,172,610 B2 | 2/2007 | Heitzmann et al. |
| 7,179,269 B2 | 2/2007 | Welch et al. |
| 7,220,269 B1 | 5/2007 | Ansel et al. |
| 7,309,318 B2 | 12/2007 | Cassell et al. |
| 7,399,307 B2 | 7/2008 | Evans et al. |
| 7,407,506 B2 | 8/2008 | Makower |
| 7,434,437 B2 | 10/2008 | Kato |
| 7,462,187 B2 | 12/2008 | Johnston et al. |
| 7,470,239 B1 | 12/2008 | Rooney et al. |
| 7,473,263 B2 | 1/2009 | Johnston et al. |
| 7,488,322 B2 | 2/2009 | Brunnett |
| 7,494,468 B2 | 2/2009 | Rabiner et al. |
| 7,494,687 B2 | 2/2009 | Cox |
| 7,507,246 B2 | 3/2009 | McGuckin et al. |
| 7,517,351 B2 | 4/2009 | Culp et al. |
| 7,575,585 B2 | 8/2009 | Goto et al. |
| 7,621,880 B2 | 11/2009 | Ryan et al. |
| 7,628,763 B2 | 12/2009 | Noriega et al. |
| 7,645,242 B1 | 1/2010 | Jalisi et al. |
| 7,645,261 B2 | 1/2010 | Hinchliffe |
| 7,655,016 B2 | 2/2010 | Demarais et al. |
| 7,744,545 B2 | 6/2010 | Aimi et al. |
| 7,762,962 B2 | 7/2010 | Mishima |
| 7,763,010 B2 | 7/2010 | Evans et al. |
| 7,776,062 B2 | 8/2010 | Besselink et al. |
| 7,780,650 B2 | 8/2010 | Frassica et al. |
| 7,794,414 B2 | 9/2010 | Rabiner et al. |
| 7,819,887 B2 | 10/2010 | McGuckin et al. |
| 7,824,345 B2 | 11/2010 | Euteneuer et al. |
| 7,862,575 B2 | 1/2011 | Tal |
| 7,878,935 B2 | 2/2011 | Lahr |
| 7,878,985 B2 | 2/2011 | Cornish et al. |
| 7,883,474 B1 | 2/2011 | Mirigian et al. |
| 8,062,317 B2 | 11/2011 | McGuckin et al. |
| 8,246,641 B2 | 8/2012 | Osborne et al. |
| 8,361,095 B2 | 1/2013 | Osborne |
| 8,393,338 B2 | 3/2013 | Wyatt |
| 8,414,543 B2 | 4/2013 | McGuckin et al. |
| 8,465,511 B2 | 6/2013 | McGuckin, Jr. |
| 8,663,259 B2 * | 3/2014 | Levine ........... A61B 17/320758 606/159 |
| 8,764,779 B2 * | 7/2014 | Levine ........... A61B 17/320758 606/159 |
| 9,023,070 B2 * | 5/2015 | Levine ........... A61B 17/320758 606/159 |
| 9,282,992 B2 * | 3/2016 | Levine ........... A61B 17/320758 |
| 9,700,346 B2 | 7/2017 | Levine |
| 9,795,406 B2 | 10/2017 | Levine |
| 10,064,645 B2 * | 9/2018 | Levine ........... A61B 17/320758 |
| 2001/0009980 A1 | 7/2001 | Richardson et al. |
| 2001/0031981 A1 | 10/2001 | Evans |
| 2002/0007190 A1 * | 1/2002 | Wulfman ....... A61B 17/320725 606/167 |
| 2002/0013548 A1 | 1/2002 | Hinchliffe |
| 2002/0058956 A1 | 5/2002 | Honeycutt et al. |
| 2002/0095102 A1 | 7/2002 | Winters |
| 2002/0143350 A1 | 10/2002 | Heitzmann et al. |
| 2002/0165567 A1 | 11/2002 | Shiber |
| 2002/0173812 A1 | 11/2002 | McGuckin, Jr. |
| 2003/0023190 A1 | 1/2003 | Cox |
| 2003/0139750 A1 | 7/2003 | Shinozuka et al. |
| 2003/0181828 A1 | 9/2003 | Fujimato |
| 2003/0191483 A1 | 10/2003 | Cooke et al. |
| 2003/0216668 A1 | 11/2003 | Howland |
| 2004/0030266 A1 | 2/2004 | Murayama |
| 2004/0073243 A1 | 4/2004 | Sepetka et al. |
| 2004/0167436 A1 | 8/2004 | Reynolds |
| 2004/0167442 A1 | 8/2004 | Shireman |
| 2004/0167443 A1 | 8/2004 | Shireman |
| 2004/0181175 A1 | 9/2004 | Clayman |
| 2004/0193073 A1 | 9/2004 | DeMello |
| 2005/0004517 A1 | 1/2005 | Courtney et al. |
| 2005/0054951 A1 | 3/2005 | Parins |
| 2005/0055040 A1 | 3/2005 | Tal |
| 2005/0080478 A1 | 4/2005 | Barongan |
| 2005/0119678 A1 | 6/2005 | O'Brien |
| 2005/0137501 A1 | 6/2005 | Euteneuer et al. |
| 2005/0240146 A1 | 10/2005 | Nash et al. |
| 2006/0074441 A1 | 4/2006 | McGuckin, Jr. et al. |
| 2006/0106407 A1 | 5/2006 | McGuckin, Jr. et al. |
| 2006/0142793 A9 | 6/2006 | Prudnikov et al. |
| 2006/0276814 A1 | 12/2006 | Omata et al. |
| 2007/0060911 A1 | 3/2007 | Webster et al. |
| 2007/0088323 A1 | 4/2007 | Campbell et al. |
| 2007/0161963 A1 | 7/2007 | Smalling |
| 2007/0219484 A1 | 9/2007 | Straub |
| 2007/0239182 A1 | 10/2007 | Glines et al. |

(56) References Cited

U.S. PATENT DOCUMENTS

| | | |
|---|---|---|
| 2007/0250096 A1 | 10/2007 | Yamane et al. |
| 2007/0272269 A1* | 11/2007 | Wyatt .................. A45D 40/265 132/320 |
| 2007/0282359 A1 | 12/2007 | Tal |
| 2007/0282539 A1 | 12/2007 | Metcalf |
| 2008/0091223 A1 | 4/2008 | Pokorney et al. |
| 2008/0103516 A1 | 5/2008 | Wulfman et al. |
| 2008/0188793 A1 | 8/2008 | Kozak et al. |
| 2008/0208233 A1 | 8/2008 | Barnes et al. |
| 2008/0228208 A1 | 9/2008 | Wulfman et al. |
| 2008/0300532 A1 | 12/2008 | Bonnette et al. |
| 2008/0319462 A1 | 12/2008 | Montague et al. |
| 2009/0018567 A1 | 1/2009 | Escudero et al. |
| 2009/0048537 A1 | 2/2009 | Lydon et al. |
| 2009/0062773 A1 | 3/2009 | Cornish |
| 2009/0112127 A1 | 4/2009 | Keating et al. |
| 2009/0138031 A1 | 5/2009 | Tsukernik |
| 2009/0143702 A1 | 6/2009 | Fleischhacker |
| 2009/0209987 A1 | 8/2009 | Mathews et al. |
| 2009/0227900 A1 | 9/2009 | Kim et al. |
| 2009/0234378 A1 | 9/2009 | Escudero et al. |
| 2009/0270791 A1 | 10/2009 | Todd |
| 2009/0306546 A1 | 12/2009 | Knapp |
| 2009/0318835 A1 | 12/2009 | Ressemann et al. |
| 2010/0004561 A1 | 1/2010 | Nabeshima |
| 2010/0004562 A1 | 1/2010 | Jalisi et al. |
| 2010/0049225 A1 | 2/2010 | To et al. |
| 2010/0069794 A1 | 3/2010 | Uihlein |
| 2010/0094201 A1 | 4/2010 | Mallaby |
| 2010/0168619 A1 | 7/2010 | Elsesser |
| 2010/0211087 A1 | 8/2010 | Osborne |
| 2010/0222786 A1 | 9/2010 | Kassab |
| 2010/0249655 A1 | 9/2010 | Lemon |
| 2010/0305592 A1 | 12/2010 | McGuckin et al. |
| 2010/0312263 A1 | 12/2010 | Moberg et al. |
| 2011/0004107 A1 | 1/2011 | Rosenthal et al. |
| 2011/0077673 A1 | 3/2011 | Grubac et al. |
| 2011/0077674 A1 | 3/2011 | Sullivan et al. |
| 2011/0087254 A1 | 4/2011 | Welty |
| 2011/0112563 A1 | 5/2011 | To et al. |
| 2011/0125176 A1 | 5/2011 | Yates et al. |
| 2011/0230862 A1 | 9/2011 | Segner et al. |
| 2011/0282370 A1 | 11/2011 | Levine et al. |
| 2012/0035634 A1 | 2/2012 | McGuckin et al. |
| 2012/0116429 A1 | 5/2012 | Levine et al. |
| 2012/0239066 A1 | 9/2012 | Levine et al. |
| 2013/0267844 A1 | 10/2013 | McGuckin, Jr. |
| 2014/0148830 A1 | 5/2014 | Bowman |
| 2014/0148831 A1* | 5/2014 | Levine ........... A61B 17/320758 606/159 |
| 2014/0324081 A1* | 10/2014 | Levine ........... A61B 17/320758 606/159 |
| 2016/0235433 A1 | 8/2016 | Levine |
| 2017/0296220 A1 | 10/2017 | Levine |

FOREIGN PATENT DOCUMENTS

| | | |
|---|---|---|
| EP | 0358825 | 9/1988 |
| EP | 0409372 | 2/1990 |
| JP | 56020839 | 2/1981 |
| JP | 03-186256 | 8/1991 |
| JP | 06-197899 | 7/1994 |
| WO | WO-9505209 | 2/1995 |
| WO | WO-1998/38926 | 9/1998 |
| WO | WO-9923958 | 5/1999 |
| WO | WO-1999/56638 | 11/1999 |
| WO | WO-2000/32265 | 6/2000 |
| WO | WO-2009/029430 | 3/2009 |

* cited by examiner

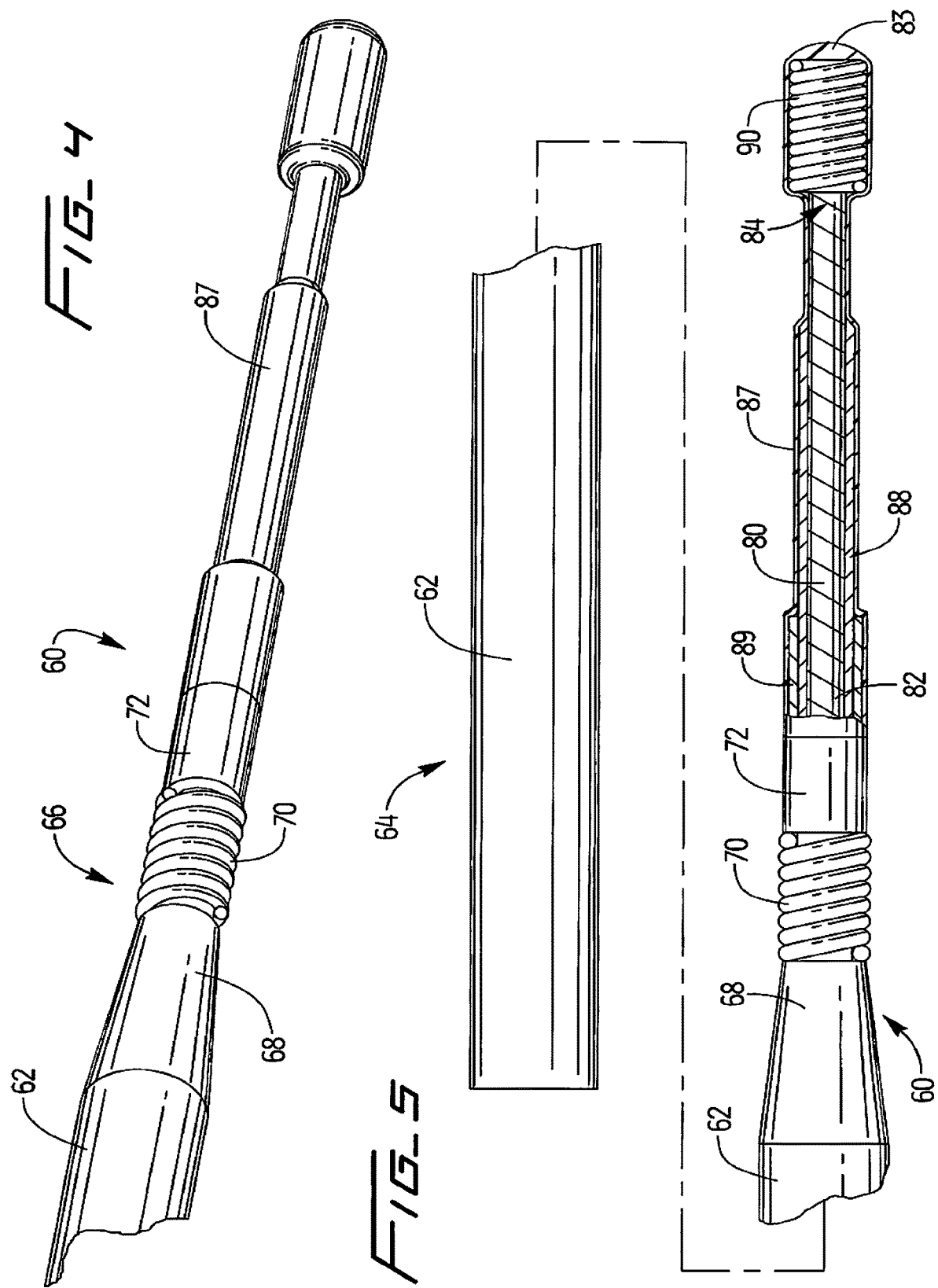

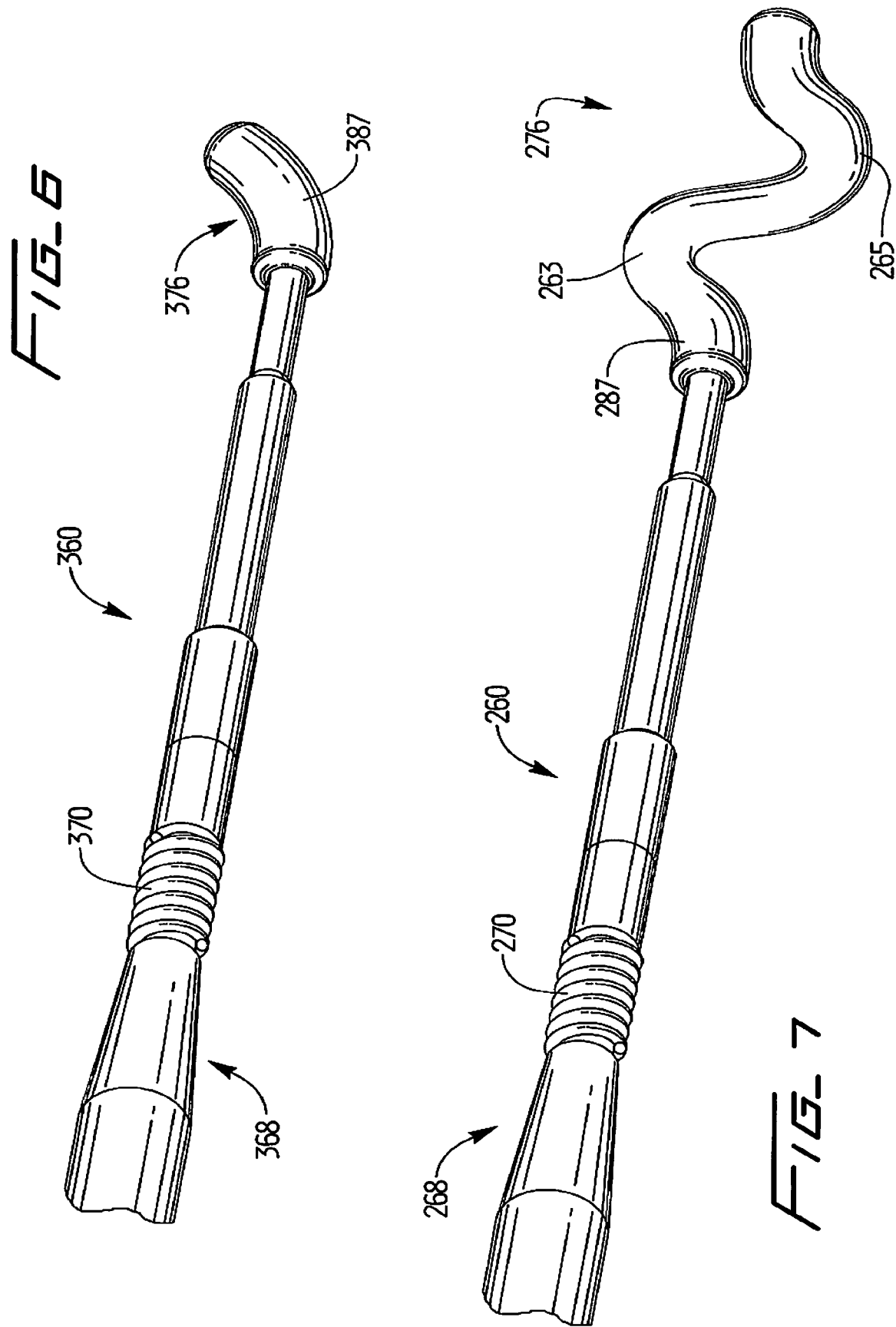

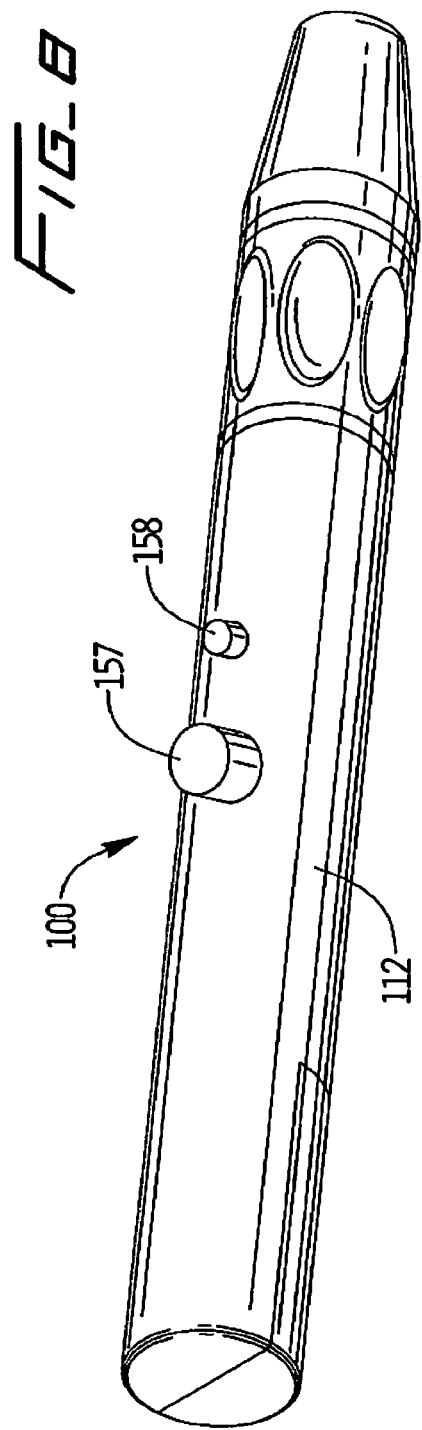
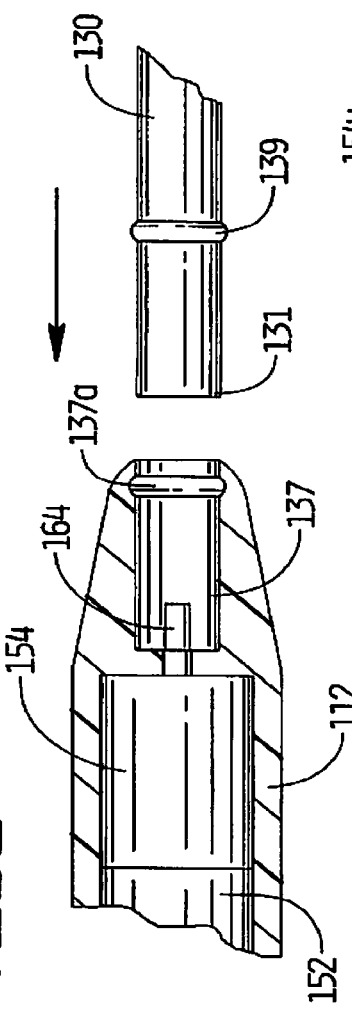
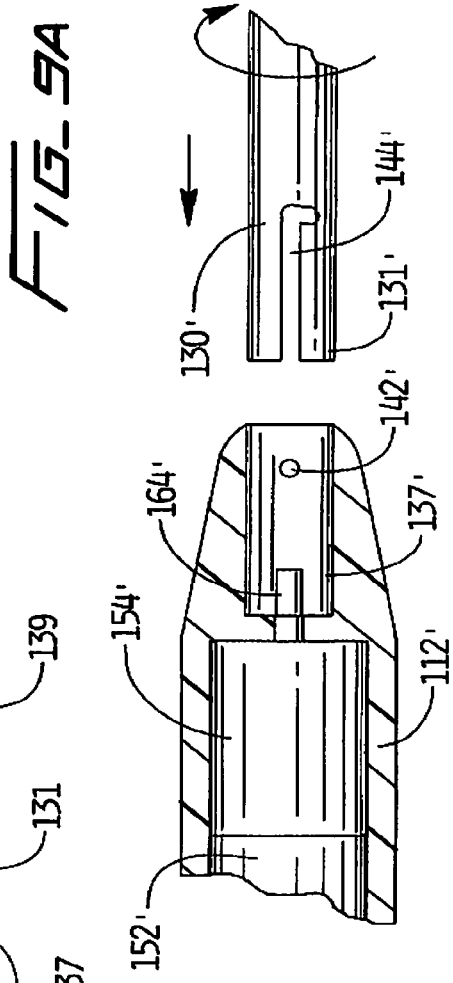

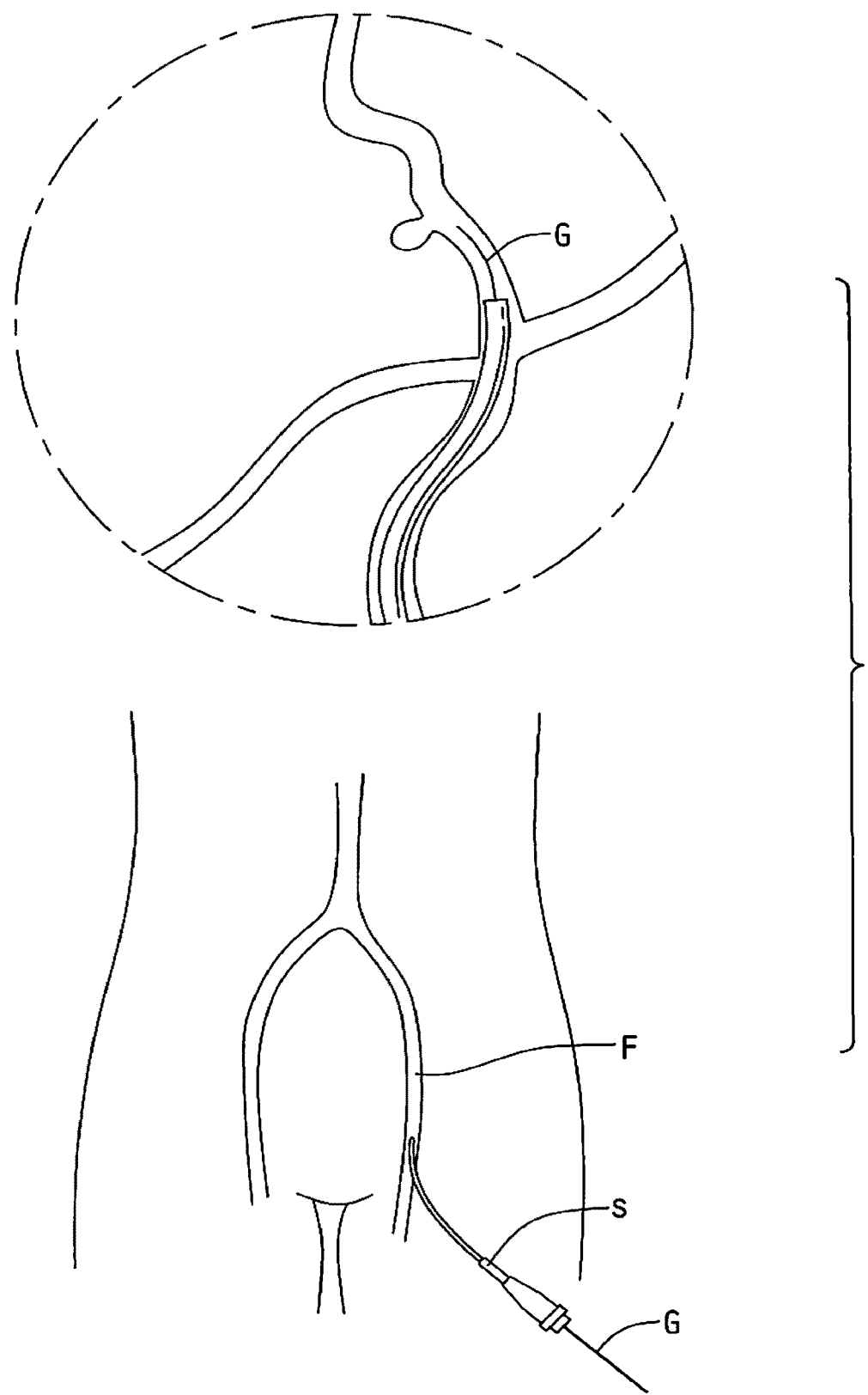
FIG_12

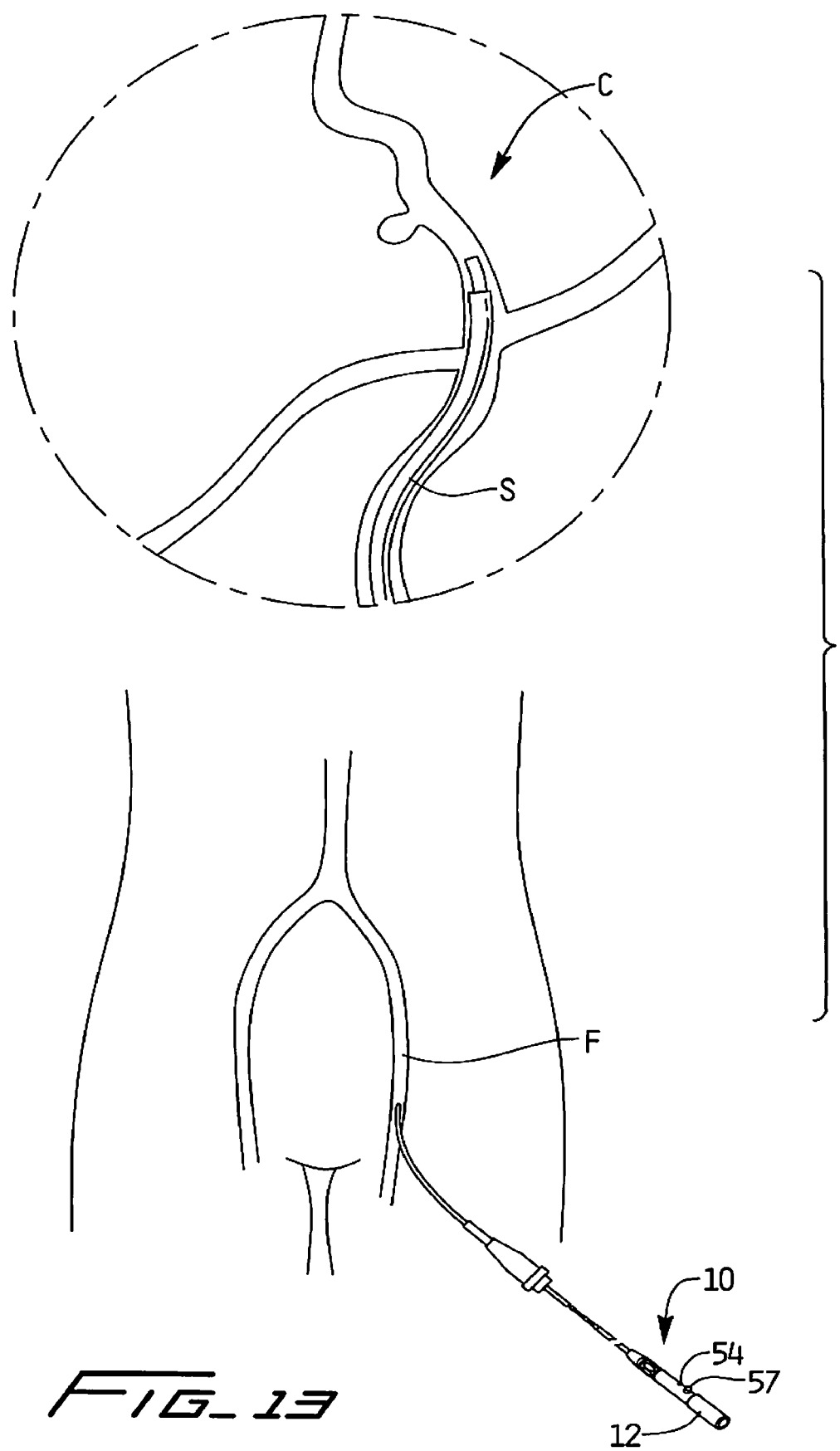
FIG_13

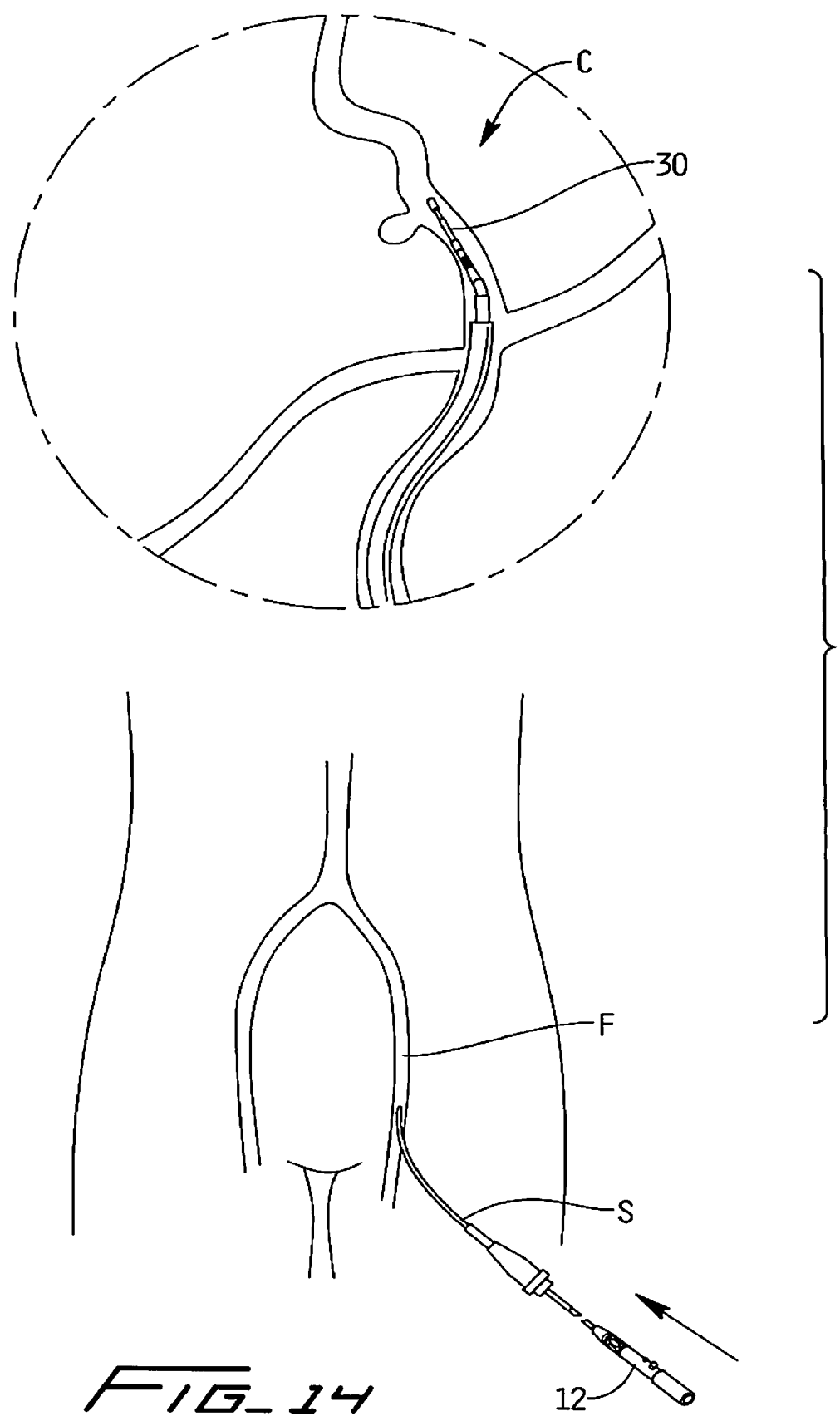
FIG_14

ROTATIONAL THROMBECTOMY WIRE

This application is a continuation of co-pending U.S. application Ser. No. 14/170,577, filed Feb. 1, 2014, which is a divisional of U.S. application Ser. No. 13/095,329, filed Apr. 27, 2011, now U.S. Pat. No. 8,663,259, which claims priority from provisional application Ser. No. 61/334,412, filed May 13, 2010. The entire contents of each of these applications are incorporated herein by reference.

BACKGROUND

Technical Field

This application relates to a rotational thrombectomy wire for clearing thrombus from native vessels.

Background of Related Art

There have been various attempts to break up clots and other obstructing material in grafts or native vessels. One approach is through injection of thrombolytic agents such as urokinase or streptokinase. These agents, however, are expensive, require lengthier hospital procedures and create risks of drug toxicity and bleeding complications as the clots are broken.

Other approaches to breaking up clots involve mechanical thrombectomy devices. For example, U.S. Pat. No. 5,766,191 discloses a cage or basket composed of six memory wires that expand to press against the inner lumen to conform to the size and shape of the lumen. This multiple wire device is expensive and can be traumatic to the graft, possibly causing damage, since as the basket rotates, the graft is contacted multiple times by the spinning wires. Other risks associated with the basket include the possibility of catching onto the graft itself and tearing the graft as well as catching and tearing the suture at the anastomotic site. Additionally, the basket can become filled with a clot which would then require time consuming withdrawal of the basket, cleaning the basket and reinserting it into the lumen. This device could be traumatic if used in the vessel, could denude endothelium, create vessel spasms and has the potential for basket and drive shaft fracture.

U.S. Pat. No. 6,090,118, incorporated herein by reference in its entirety, discloses a wire rotated to create a standing wave to break-up or macerate thrombus. The single wire is less traumatic than the aforedescribed basket device since it minimizes contact with the graft wall while still effectively mechanically removing thrombotic material.

U.S. Pat. No. 7,037,316 discloses another example of a rotational thrombectomy wire for breaking up clots in grafts. The thrombectomy wire has a sinuous shape at its distal end and is contained within a sheath in a substantially straight non-deployed position. When the sheath is retracted, the distal portion of the wire is exposed to enable the wire to return to its non-linear sinuous configuration. The wire is composed of two stainless steel wires wound side by side with an elastomeric tip at the distalmost end. Actuation of the motor causes rotational movement of the wire, creating a wave pattern, to macerate thrombus. Thus, it provides the additional advantages of increased reliability and consistency in creating the wave pattern since the wave pattern created by the standing wave of the '118 patent will depend more on the rotational speed and the stiffness of the wire. Additionally, the sinuous configuration enables creation of a wave pattern at a lower rotational speed.

Although the sinuous wire of the '316 patent is effective in proper clinical use to macerate thrombus in dialysis grafts, it is not best suited for use in native vessels. U.S. Pat. No. 7,819,887, (Publication No 2006/0106407) the entire contents of which are incorporated herein by reference, discloses a thrombectomy wire better suited for use in native vessels (and can also be used for deep vein thrombosis and pulmonary embolisms).

In neurovascular thrombectomy procedures, the thrombectomy wire needs to navigate small tortuous vessels. That is, the wire is inserted through femoral artery and then must navigate small and tortuous vessels as it is advanced to the smaller cerebral arteries of the brain. Within the brain, the carotid and vertebrobasilar arteries meet to form the circle of Willis. From this circle, other arteries, e.g., the anterior cerebral artery, the middle cerebral artery and the posterior cerebral artery, arise and travel to various parts of the brain. Clots formed in these cerebral arteries can cause stroke and in certain instances death of the patient.

Due to the size and curves of the vessels en route to the cerebral arteries from the femoral artery, as well as the size and structure of the cerebral arteries themselves, access is difficult. If the thrombectomy device is too large then navigation through the small vessels, which can be as small as 1 mm, would be difficult. Also, if the device is too stiff, then it can damage the vessel walls during insertion. On the other hand, if the device is too flexible, it will lack sufficient rigidity to be advanced around the vessel curves and can be caught in the vessel. Consequently, it would be advantageous to provide a thrombectomy device for breaking cerebral clots and other obstructing material that strike the optimal balance of flexibility and stiffness, thus effectively having the insertability of a tracking guidewire while enabling high speed rotation to effectively macerate clots or other material without damaging vessels.

It would also be advantageous in certain instances to provide a separable thrombectomy wire and motor for connection by the user, which can ease insertion of the wire and enable replacement of different motors and/or batteries.

SUMMARY

The present invention advantageously provides in one aspect a rotational thrombectomy wire for breaking up vascular thrombus or other obstructive material. The wire comprises a core having a proximal portion and a distal portion, the distal portion having a smaller diameter than the proximal portion. A cable extends distally of the core and has a first covering material positioned external thereof. A first coil is attached to a distal portion of the cable, the first coil having a diameter larger than a diameter of the cable and having a second covering material positioned thereover. The wire is rotatable by a motor.

In one embodiment, the first coil has a sinuous shape. In another embodiment the first coil has a J-tip.

In some embodiments, a second coil is positioned over a region of the distal portion of the cable.

In some embodiments, the cable has multiple layers of polymeric material positioned thereover, wherein the layers create a larger diameter proximal region. The cable can have variable stiffness such that a distal portion of the cable has a lower stiffness than a proximal portion. A hypotube can be provided to couple the cable to the core.

In some embodiments, the wire has a connector at a proximal portion for connection by the user to a handle containing a motor.

In another aspect, the present invention provides a thrombectomy apparatus for breaking up vascular thrombus or other obstructive material comprising a wire having a core having a proximal portion and a distal portion. The distal portion has a smaller diameter than the proximal portion. A cable extends distally of the core. A first coil is attached to the distal portion of the cable. The first coil has a diameter larger than a diameter of the cable and has a first covering material positioned thereover. The wire is rotatable by a motor. A housing contains a motor to rotate the wire. The wire is connectable to the motor by the user.

The apparatus can include an adjustment mechanism to adjust the speed of the motor. A gear reducer can be connected to the motor and a coupling tube can extend from the gear reducer to detachably connect the thrombectomy wire to the motor.

In some embodiments, a hypotube can connect the cable to the core.

In some embodiments, the wire is connectable to the motor coupler by a bayonet connector; in other embodiments it is connectable to the motor coupler by a friction fit.

In some embodiments, the apparatus includes a sheath extending from the housing and slidable between a distal position to cover the first coil to a proximal position to expose the first coil.

In another aspect, the present invention provides a method for removing thrombus in a cerebral artery of a patient comprising the steps of:

introducing a guidewire into the femoral artery;

inserting the guidewire through the vascular system in the cerebral artery;

inserting a catheter tube over the guidewire into the cerebral artery;

removing the guidewire;

placing an introducer at the proximal end of the catheter tube;

inserting a thrombectomy wire through the introducer and into the catheter tube, the thrombectomy wire having a coiled tip with a covering thereover;

advancing the thrombectomy wire to the cerebral artery;

operatively coupling a motor to the proximal end of the thrombectomy wire; and activating the motor to rotate the thrombectomy wire to macerate thrombus in the cerebral artery.

In one embodiment, the step of inserting the thrombectomy wire to the cerebral artery includes the step of inserting the thrombectomy wire into the circle of Willis.

BRIEF DESCRIPTION OF THE DRAWINGS

Preferred embodiment(s) of the present disclosure are described herein with reference to the drawings wherein:

FIG. 4 is an enlarged view of the distal portion of the thrombectomy apparatus of FIG. 1;

FIG. 5 is a longitudinal cross-sectional view of the apparatus shown in FIG. 4;

FIG. 6 is a perspective view of an alternate embodiment of the thrombectomy apparatus of the present invention having a curved tip;

FIG. 7 is a perspective view of another alternate embodiment of the thrombectomy apparatus of the present invention having a sinuous tip;

FIG. 8 is a perspective view of an alternate embodiment of the handle portion of a thrombectomy apparatus;

FIG. 9 is a cross-sectional view illustrating connection of the thrombectomy wire to the handle portion of FIG. 8 in accordance with one embodiment of the present invention, the handle shown in cross-section;

FIG. 9A is a cross-sectional view similar to FIG. 9 showing an alternate embodiment of a connector for the wire and handle portion;

FIG. 12 illustrates insertion of an introducer sheath through the femoral artery and into the cerebral artery over a tracking guidewire;

FIG. 13 illustrates insertion of the thrombectomy apparatus through the introducer sheath and into the circle of Willis; and FIG. 14 illustrates continued advancement of the thrombectomy wire of FIG. 13 to deploy the distal portion of the wire in the circle of Willis.

DETAILED DESCRIPTION OF PREFERRED EMBODIMENTS

Figure 1:
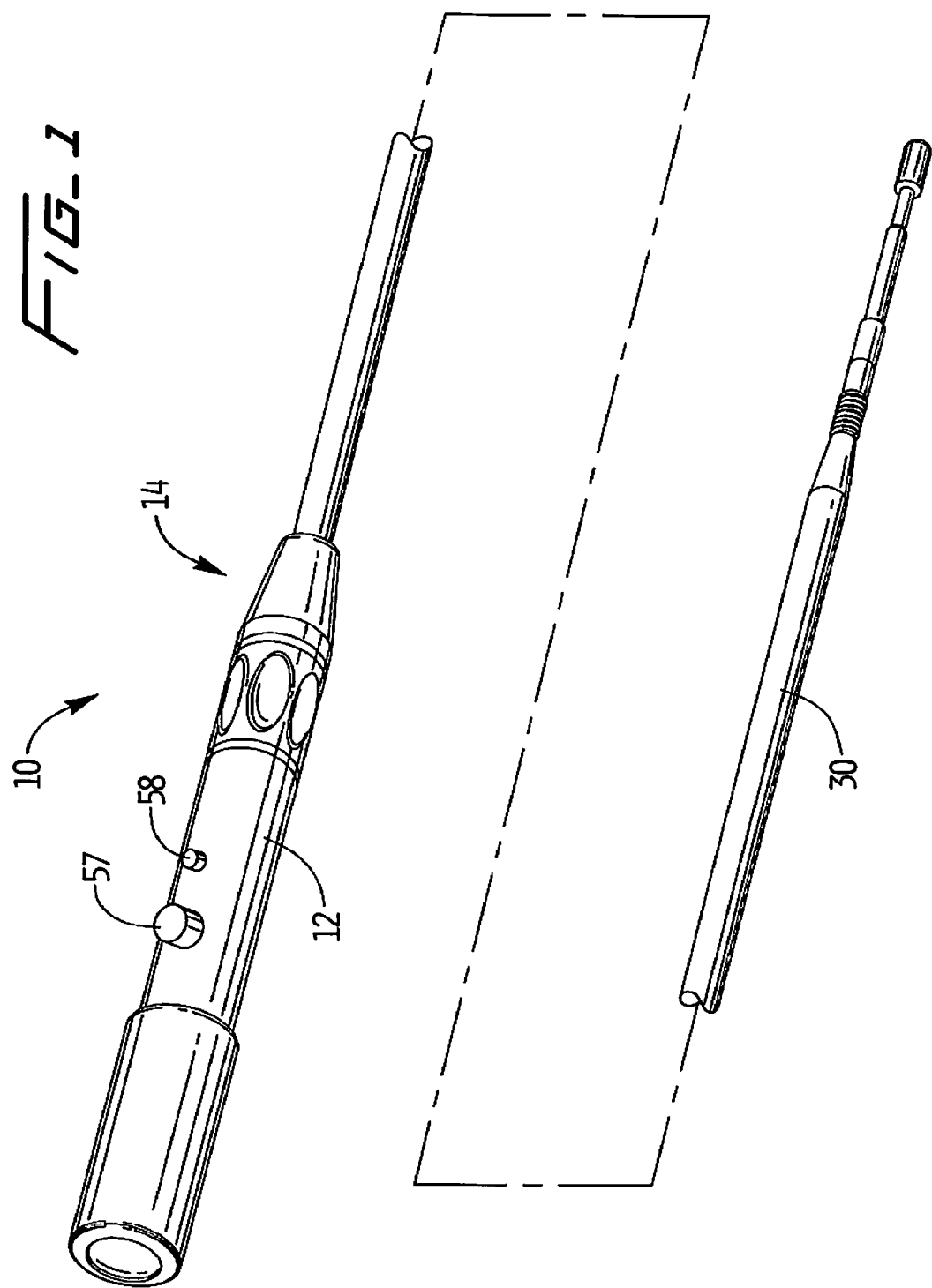
FIG. 1 is a perspective view of a first embodiment of a thrombectomy apparatus of the present invention.

Referring now in detail to the drawings where like reference numerals identify similar or like components throughout the several views, FIG. 1 illustrates a first embodiment of the thrombectomy apparatus of the present invention.

The thrombectomy apparatus of FIG. 1 is designated generally by reference numeral 10. The apparatus includes a housing 12 and a rotational thrombectomy wire 30 extending therefrom.

As discussed below, the apparatus can be inserted into a separate introducer sheath to shield the distal end portion of the wire 30 during insertion. Alternatively, the apparatus can include a sheath (not shown) extending from the housing 12 which is movable between a distal (advanced) position to cover the distal tip portion of the thrombectomy wire 30 and a proximal (retracted) position to expose the distal tip portion of the wire 30. In this version, a knob on housing 12 is operatively attached to the flexible sheath to enable sliding movement of the flexible sheath (tube) with respect to the wire 30, and can also provide rotation of the sheath. The flexible sheath can be slidable and the wire fixed axially, alternatively, the wire can be axially slidable within the stationary sheath, or both the wire and sheath can be slidable. In any case, such relative movement of the wire and sheath will enable the wire 30 to be exposed to enable removal of obstructions, such as blood clots, from the lumen of the vascular structure. The use of such sheath is also applicable to the other wires disclosed herein. An example of a slidable sheath to cover and uncover a thrombectomy wire is disclosed in U.S. Pat. No. 7,037,316, the entire contents of which are incorporated herein by reference.

It is also contemplated that the thrombectomy wire 30 (as well as the other wires disclosed herein) can be a separate component/assembly insertable into a separate sheath component/assembly either prior to insertion into the body or after the sheath is already placed in the body. In the latter, the sheath can be inserted with a placement (tracking) guidewire and then the placement guidewire removed for insertion of the thrombectomy wire 30 into the already placed sheath. This is the version shown in FIG. 1.

Figure 2:
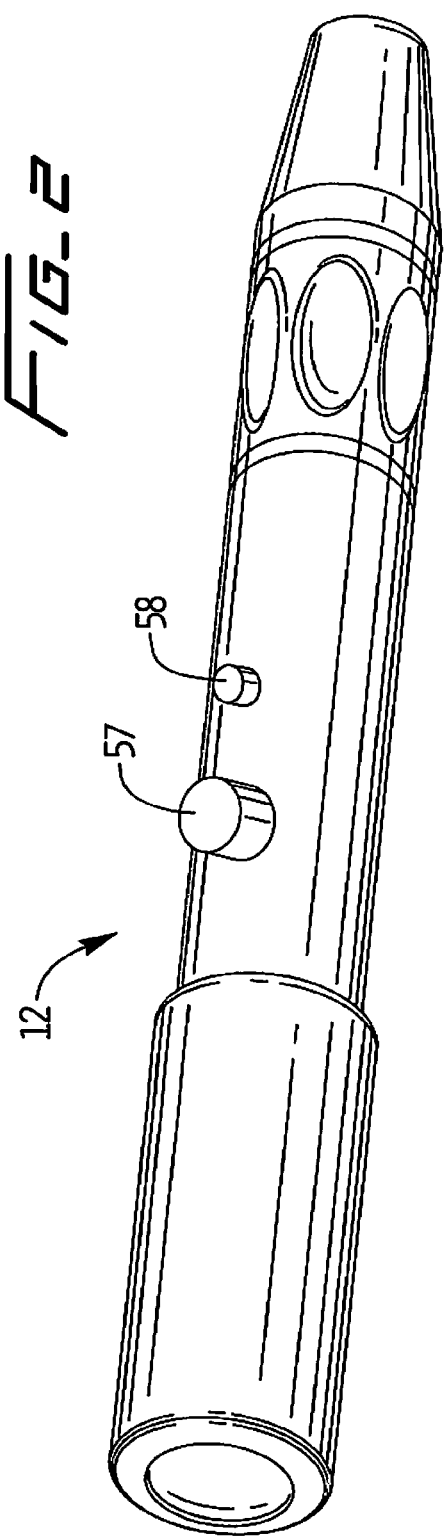
FIG. 2 is an enlarged perspective view of the housing of the apparatus of FIG. 1.
Figure 3:
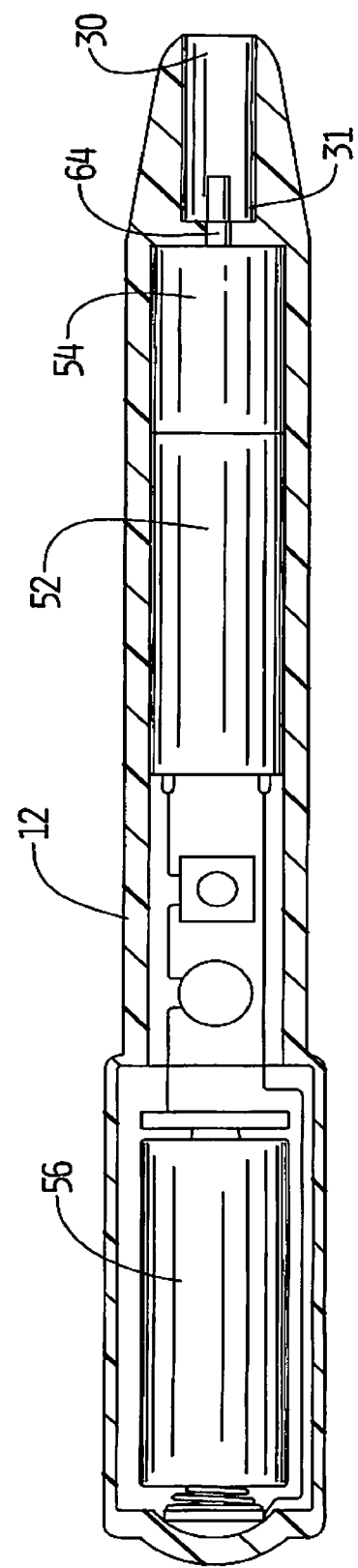
FIG. 3 is a longitudinal cross-sectional view of the housing of FIG. 2.

Turning to the housing or handle portion 12, and with reference to FIGS. 1-3, contained within housing 12 is a motor 52, a gear reducer 54, and a battery 56, such as a 3 Volt battery, for powering the motor 52. The battery 56 can be contained within a compartment in the housing 12 accessible by removing a battery door. A coupling tube 64 is connected to the speed reducing gear 54 for connection to a proximal end 31 of the thrombectomy wire 30. The gear reducer by way of example can reduce the rotational speed of the motor 52 from 15,000 rpm to 1500 rpm, 750 rpm, 150 rpm, etc. When the motor 52 is energized, the support or coupling tube 64 is rotated about its longitudinal axis, via rotation of a chuck driven by gears, thereby rotating the wire 30 about its longitudinal axis. A potentiometer 57 is wired to the motor to enable dialing the motor speed up or down to adjust the rotational speed of the thrombectomy wire 30 to adjust for various procedures and/or clot locations and sizes. In a preferred embodiment, the potentiometer is used as a two terminal variable resistor, i.e. a rheostat, by not connecting the third terminal. In this manner, in the initial position, the motor speed is at the desired minimum and rotation of a knob 57 (or in alternate embodiments sliding of a knob or actuation of another type of actuator) progressively increases the motor speed. An on/off switch 58 extending from the housing 12 is electrically connected to the motor 52 to turn on the motor 52 to activate the apparatus, i.e. rotate the wire 30.

Further details of the internal components which can be utilized to connect and rotate the wire are illustrated and described in U.S. Pat. No. 7,037,316, the entire contents of which have already been incorporated herein by reference. Such arrangements can also be used to connect and spin the thrombectomy wire of the other embodiments disclosed herein.

The housing 12 in alternate embodiments can be a separate unit attachable to the wire by the clinician. In such embodiments, it can be detachably connected to the thrombectomy wire, and alternatively in some embodiments it can be configured for permanent attachment once connected by the clinician. The detachable connection is shown in FIGS. 8 and 9. Apparatus 100 is identical to apparatus 10 except for the connection of the proximal end 131 of wire 130 to the housing 112. That is, the rotational thrombectomy wire 130, either after insertion to the surgical site or prior to insertion, is attached by a clinician at a proximal end 131 to coupler tube 164 which is connected to gear reducer 154. Motor 152 is within housing 112. The connection of wire 130 can be for example a friction fit as shown in FIG. 9 or a twist connect, e.g. a bayonet connection as shown in FIG. 9A, by way of example. In the friction mount, the O-ring 139 of wire 130 is seated within O-ring recess 137a of housing recess 137. In the bayonet mount, like components to FIG. 9 are labeled with "prime" designations, e.g. coupler tube 164', gear reducer 154', housing 112', motor 152' etc. The pin and slot are designated by reference numerals 142', 144', respectively; pin 142' extending in housing recess 137' and slot 144' formed in proximal end 131' of wire 130'. Note other connections are also contemplated. These attachable connections can ease insertion of the wire as the wire 130 (and 130') can be inserted in a similar manner as a tracking guidewire (without a handle) and then the handle (housing) 112 (or 112') attached after insertion of the wire 130 (or 130"). Insertion without a handle can aid introduction and manipulation of the wire since it is less cumbersome and of lighter weight than if the motor housing was attached during manipulation of the wire. Additionally, by having a detachable housing 112 (or 112'), different handles with different motor speeds and/or different batteries can be utilized by attachment to the wire 130 (or 130'). This can even be achieved during the same surgical procedure. Such connections can also be used for detachable connection of wires 260 and 360.

In some embodiments, the housing can be detached, sterilized and reused after recharging of the battery or replacing the battery.

It is also contemplated that as an alternative to a removable attachment, in certain embodiments, once attached, the wire and housing can be non-detachable (inseparable) from each other.

Housing 112 of apparatus includes knob 157 and switch 158 for actuating motor 152 which are identical to knob 57 and switch 58 of FIG. 1.

FIGS. 1, 4 and 5 illustrate the thrombectomy wire 30 (wire 60) with a distal coiled tip 90 substantially aligned with the longitudinal axis of the apparatus during both insertion and use. In alternate embodiments, the distal coiled tip is angled with respect to the longitudinal axis and thus has a non-linear configuration. For example, in FIG. 6, the wire 360 forms a J-tip which creates a standing wave upon rotation. In the embodiment of FIG. 7, the wire 260 forms a substantially sinuous shape, resembling a sine curve. These various tips are discussed in more detail below.

As noted above, these various thrombectomy apparatus disclosed herein can be provided without a sheath and inserted into an already placed sheath in the body or inserted into a sheath and then together inserted in the body. However, it is also contemplated that a sheath can be provided as part of the apparatus, operatively attached to and extending from the housing (12, 112 or 112'), to slide to cover and uncover (expose) the distal tip of the wire.

In the embodiments wherein a sheath (flexible tube) is connected to the housing and is slidable with respect to the housing 12 (or housing 112 or 112') and the thrombectomy wire, the flexible tube can also be rotatable. Sliding movement of a control mechanism such as a knob accordingly slides the flexible tube axially and rotation of the control mechanism (or a separate mechanism) accordingly rotates the flexible tube about its longitudinal axis. Sliding movement of the control mechanism exposes the rotational wire, and in the non-linear distal tip embodiments, enables the distal tip of the wire to assume its curved (non-linear) configuration of FIG. 6 or 7. Rotation of the knob can be used for example to orient the rotational wire of FIG. 6 due to the J-shaped distal end.

The flexible sheath or tube can optionally contain one or more braided wires embedded in the wall to increase the stiffness. Such braided wires would preferably extend the length of the sheath, terminating proximal of the angled tip.

In the embodiment with a sheath (flexible tube), an extension arm of a Touhy borst can be provided positioned within housing 12 (or 112, 112') having a lumen communicating with the lumen of the flexible sheath. Fluids such as imaging dye can be injected through the arm, flowing through the sheath in the space between the wire and the inner wall of the sheath, and exiting a distal opening to flow into the vessel. This imaging dye can be used to provide an indication that fluid flow has resumed in the vessel. The Touhy can contain a conventional silicone gasket which is compressed when tightened to provide a seal to prevent back flow of fluid around the support tube. An example of such extension arm is disclosed in U.S. Pat. No. 7,037,316, the entire contents of which are incorporated herein by reference. Suction can also be applied in the space between the wire and the inner wall of the sheath.

With reference to FIG. 6, the wire 360 terminates in a J-tip configuration at distal tip 376. Due to this angle, when the wire is rotated by the motor at sufficient speed at least one vibrational node is formed. Details of this creation of a standing wave are described in U.S. Pat. No. 6,090,118, the entire contents of which are incorporated herein by reference.

Wire 260 of FIG. 7 has a substantially linear portion extending through most of its length, from a proximal region, through an intermediate region, to adjacent distal region 276. At the distal region 276, wire 260 has a sinuous shape in that as shown it has a first arcuate region 263 facing a first direction (upwardly as viewed in the orientation of FIG. 7) and a second arcuate region 265, spaced longitudinally from the first arcuate region 263, facing a second opposite direction (downwardly as viewed in the orientation of FIG. 7). These arcuate regions 263, 265 form "peaks" to contact vascular structure as the wire 260 rotates. These peaks 263, 265 can be equal (symmetric) or of different heights, e.g. peak 265 extending a further distance from a longitudinal axis than peak 263. This distal portion 276 includes a coiled portion with a covering material to block the interstices of the coil similar to the covered coil of wire 60 discussed below.

When the wire 260 is fully retracted within the sheath (either the introducer sheath or in other embodiments within the sheath extending from the apparatus housing), the curved regions of the wire 260 are compressed so the distal region 276 is contained in a substantially straight or linear non-deployed configuration. This covering of the wire 260 facilitates insertion through an introducer sheath and manipulation within the vascular structure. When the flexible sheath is retracted by proximal axial movement, or the wire is advanced with respect to the sheath or both are moved with respect to each other, such relative movement causes the distal region 276 of the wire 260 to be exposed to enable the wire 260 to return to its non-linear substantially sinuous configuration shown in FIG. 7 for rotation about its longitudinal axis within the lumen of the vessel. Note that the term relative movement of the sheath and wire encompasses movement of one of these components or both of these components.

In an embodiment of the coiled tip being composed of shape memory material, the memorized configuration is sinuous or S-shape as in FIG. 7 or J-shaped as in FIG. 6. In the softer state within the sheath, the wire is in a substantially linear configuration. This state is used for delivering the wire to the surgical site. When the wire is exposed to warmer body temperature, the tip transforms to its austenitic state, assuming the S-shaped memorized configuration. The coiled tip can alternatively be a radiopaque coil/polymer pre-shaped to an "S".

Details of the wire 60, which corresponds to wire 30, will now be described with reference to FIGS. 1-5. These details are the same for wire 130 and 130' of FIGS. 9 and 9A, the only difference being its proximal end connection to the motor coupler. These details are also the same for wires 260 and 360, the only difference being that instead of the distal coiled tip being substantially straight (linear) in the deployed position, the distal tips are curved in a sinuous configuration or a J-configuration, respectively, and their overall lengths may differ. For convenience, details will be discussed with reference to wire 60. Like components in wires 260 and 360 to wire 60 are labeled in the "200 series" and the "300 series", respectively, for convenience. Note the distal coil of wires 260 and 360 underlies the covering material 287, 387, respectively, which blocks the interstices.

Wire 60 has a core 62 having a proximal portion 64 and a distal portion 66. Transition region 68 is tapered distally so that the diameter of the distal portion 66 of core 62 is less than the diameter of the proximal portion 64. In one embodiment the core is a solid material made of a nickel titanium alloy, although other materials are also contemplated. The core can also be formed from a hypotube with a tapered body attached, e.g. welded, to the distal end of the hypotube. Distally of the taper 68, the core can have a uniform diameter portion extending distally thereof.

Overlying distal portion 66 of the core 62 is coil 70, preferably composed of stainless steel, although other materials are contemplated. This coil functions to increase the diameter to increase the torsional stiffness/rigidity of the wire for pushability.

The core 62 is tapered to accommodate connection to cable 80. Hypotube 72 is positioned over the distalmost end of the core 62 and is attached thereto by a number of methods, including but not limited to, soldering welding or crimping.

Extending distally from hypotube 72, and attached thereto, is a cable 80. Thus, hypotube 72 is positioned over a proximal portion of cable 80, and functions to couple the cable 80 to the core 62. A distal coil 90 is attached over a distal end of cable 80. The cable 80 in one embodiment has a variable stiffness such that the proximal portion 82 is stiffer, e.g. has a tighter braid, than a distal portion 84 to increase the flexibility of the distal portion 84. Various covering materials, e.g. coating, jackets and/or shrink wraps, can be used as an alternative or in addition to vary the stiffness of the cable 80. A polymer coating(s) and/or jacket(s) can be placed external of the cable 80. That is, it can be placed over at least a portion of the cable 80 to cover the interstices in the cable 80. In one embodiment, a urethane jacket 88 is placed over the cable 80, a PTFE jacket 87 is placed over the urethane jacket 88, and a Pebax jacket 89 is placed over the jacket 88 at a proximal portion of the cable 80, underlying the PTFE jacket 87 and overlying jacket 88. In this manner, the cable 80 is "beefed up" at a proximal portion to provide a smoother transition from the hypotube 72 which is of larger diameter as well as to increase the stiffness of the cable 80. Note the coating or jacket 87 can extend to the distalmost end of the wire 60, extending along the length of the cable 80 and covering the distal surface of the coiled tip 90 as shown at region 83. The distal end of the jacket 88, in the illustrated embodiment, terminates proximally of coil 90 and thus extends only over a portion of cable 80. The jacket 87 or another covering material can optionally be placed over the hypotube 72 and proximal coil 70.

In an alternate embodiment, the PTFE jacket 87 is positioned over the distal end of the cable 80 and over the distal coil 90, but not over the proximal region of the cable 80. By way of example, the PTFE jacket 87 can extend for about 6 inches, although other lengths are contemplated. A Pebax, Nylon or other material can be placed over the proximal portion of the cable 80 and over the hypotube 72 and proximal coil 70 which is positioned over the reduced diameter portion of the core 62 (proximal to hypotube 72).

Coil 90, forming a coiled tip, is positioned over a distal tip of the cable 80. In one embodiment, the coiled tip 90 has a linear configuration in the deployed/uncovered position (see FIG. 1). In an alternate embodiment, the coiled tip has a J-tip configuration, as shown for example in FIG. 6. In another embodiment, shown for example in FIG. 7, the coiled tip has a substantially sinuous configuration. In each of these embodiments, a covering such as a jacket, shrink wrap or coating preferably covers the coil such as the coverings described above. The other coverings described above are also applicable to these wires.

By way of example only, the components of wire 60 can have the approximate dimensions set forth in the table below. It should be understood that these dimensions are provided by way of example as other dimensions are also contemplated. These are also approximate values.

| COMPONENT | APPROXIMAT OUTER DIAMETER | APPROXIMATE LENGTH |
|---|---|---|
| Core 62 (proximal non tapered portion) | .016 inches | 139.5 cm |
| Core tapered portion | .016 inches to .0095 inches | 11.7 cm |
| Proximal coil 70 | .016 inches | 4.4 cm |
| Hypotube 72 | .013 inches | .2 cm |
| Cable 80 | .006 inches | 39.2 cm |
| Jacket 88 | .002 inches | 15.3 cm |
| Jacket 87 | .0017 inches | 39.2 cm |
| Jacket 89 | .002 inches | 9 cm |
| Distal coil 90 | .013 inches | 1.2 cm |

The covering material, e.g. coating, jackets, and or shrink wraps, helps to prevent bending or knotting of the wire which could otherwise occur in native vessels. The covering also increases the torsional strength of the wire and also strengthens the wire to accommodate spasms occurring in the vessel. The coating 87 (and 287, 387) also blocks the interstices of the coil 90 to provide a less abrasive surface. The various coating and/or jackets and/or shrink wrap can be made of PET, Teflon, Pebax, polyurethane or other polymeric materials. The material helps to prevent the native vessel from being caught in the coil 90 and reduces vessel spasms.

Figure 11:
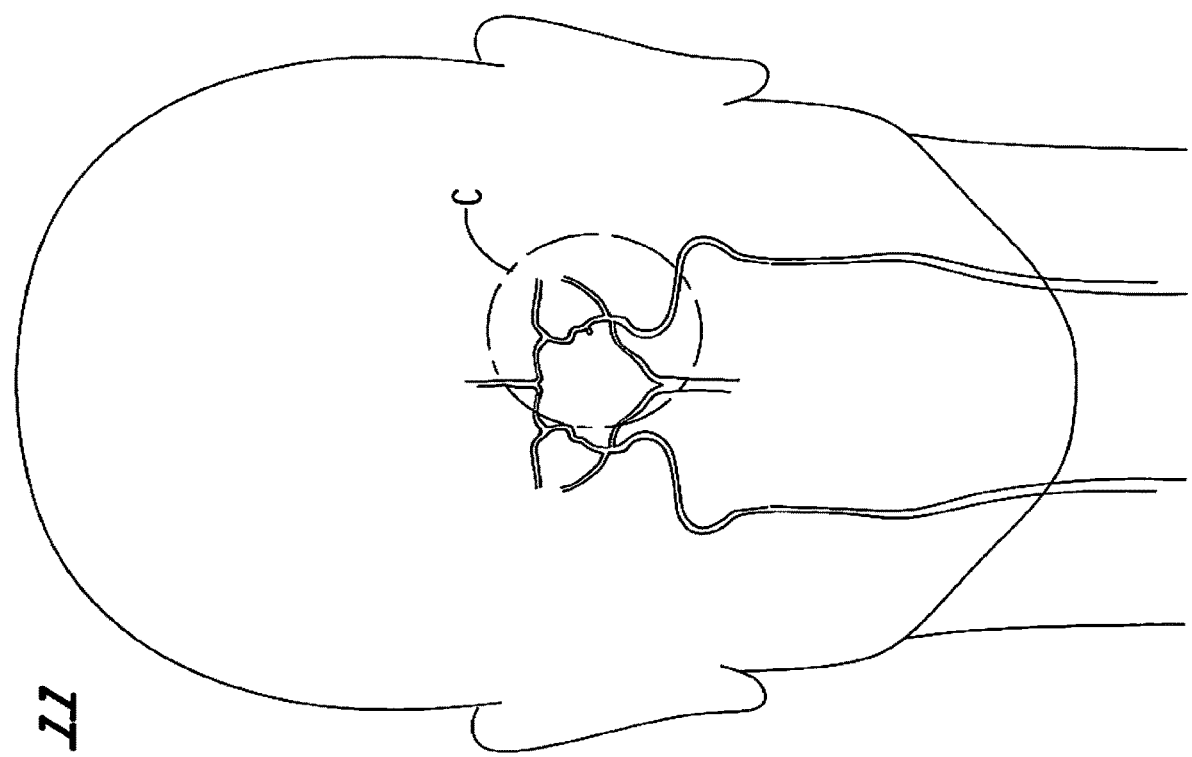
FIG. 11 is a front anatomical view showing select cerebral arteries, including the circle of Willis.
Figure 10:
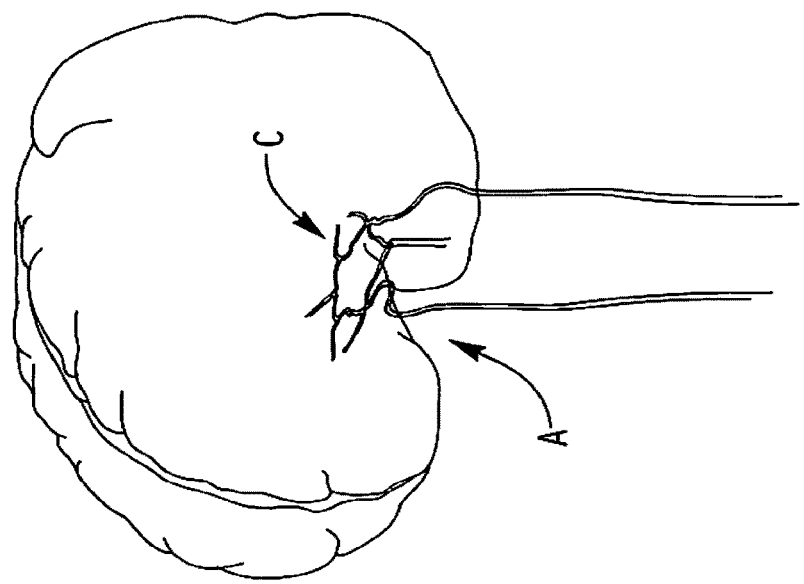
FIG. 10 is an anatomical view showing select cerebral arteries.

In use, which by way of example is shown and described with respect to the embodiment of FIGS. 1-5 but the other wires described herein would be used in the same fashion, an access sheath S is inserted into the vessel over a guidewire G in the femoral artery F and located via imaging. The sheath S is advanced to the desired site through the vascular system into the cerebral arteries A, and into the Circle of Willis C (see FIGS. 10-12). Once at the site, the guidewire G is withdrawn and the thrombectomy apparatus 10 is inserted through the sheath S (FIG. 13). An introducer tube can be utilized, placed into a proximal end of the sheath S to facilitate introduction of the wire 30 through the sheath S. Once the distal end of the wire is at the site exposed from the sheath (see FIG. 14) switch 58 on housing 12 is actuated to turn on the motor thereby causing wire 30 to rotate about its longitudinal axis. The knob 57 can be turned to dial up the motor speed. Note that if non-linear tip wires are utilized such as wires 360 or 260 of FIGS. 6, and 7, when exposed as in the position of FIG. 14, they would move to their non-linear configuration, i.e. J-shape or sinuous shape, respectively.

It should be appreciated that if a user attachable wire connection is utilized, after the position of FIG. 13 or FIG. 14, a motor housing could be connected to the wire to operatively couple the proximal end of the wire to the motor as described above. In the illustration of FIGS. 13 and 14, the motor housing is already attached, either by the attachable connection as described above or due to the housing and wire provided as a single already connected assembly which may be non-detachable.

The introducer sheath can optionally have side ports for aspirating the small particles macerated by the thrombectomy wires described herein.

Note the apparatus could include a sheath connected to the housing as described above so that the method would include the additional step of relative movement of the wire and sheath to expose the wire within the vessel.

A delivery sheath can be provided which includes a balloon to block blood flow and allow aspiration in the blocked space.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A rotational neurovascular thrombectomy wire for breaking up vascular thrombus or other obstructive material in a cerebral artery, the thrombectomy wire comprising a core having a proximal portion and a distal portion, a cable extending distally of the core and a hypotube coupling the cable to the core, the cable having a first diameter and the hypotube having a second diameter greater than the first diameter, at least a first covering material positioned over the cable to provide a smoother transition from the hypotube to the cable and increase the stiffness of the cable, the wire insertable into the cerebral artery and rotatable by a motor to macerate cerebral clots or other obstructive material in the cerebral artery.

2. The neurovascular thrombectomy wire of claim 1, further comprising a second covering material over the first covering material.

3. The neurovascular thrombectomy wire of claim 2, wherein the second covering material comprises a polymer jacket.

4. The neurovascular thrombectomy wire of claim 2, wherein the cable has a third covering material.

5. The neurovascular thrombectomy wire of claim 4, the third covering material is positioned between the cable and the second covering material.

6. The neurovascular thrombectomy wire of claim 4, wherein a distal coil is positioned over a distal end of the cable, and the third covering material terminates proximal of the distal coil.

7. The neurovascular thrombectomy wire of claim 2, wherein a distal coil is positioned over a distal end of the cable, and the second covering material extends over the distal coil.

8. The neurovascular thrombectomy wire of claim 1, further comprising a first coil positioned over the distal portion of the core to increase rigidity for pushablility through the cerebral artery.

9. The neurovascular thrombectomy wire of claim 1, wherein the core has a tapered region at a section coupled to the hypotube so the hypotube is positioned over the tapered region.

10. The neurovascular thrombectomy wire of claim 9, further comprising a first coil positioned over the distal portion of the core to increase stiffness of the wire.

11. The neurovascular thrombectomy wire of claim 10, wherein the first coil is positioned proximal of the hypotube.

12. The neurovascular thrombectomy wire of claim 1, wherein a distal coil is positioned over a distal end of the cable, a distal portion of the wire including the distal coil having a sinuous shape.

13. The neurovascular thrombectomy wire of claim 1, wherein the first covering material comprises a polymer jacket.

14. The neurovascular thrombectomy wire of claim 1, wherein a proximal portion of the cable is stiffer than a distal portion of the cable.

15. A rotational neurovascular thrombectomy wire for breaking up vascular thrombus or other obstructive material in a cerebral artery, the thrombectomy wire comprising a core having a proximal portion and a distal portion, a cable extending distally of the core and a hypotube coupling the cable to the core, the wire insertable into the cerebral artery and rotatable by a motor to macerate cerebral clots or other obstructive material, the wire having a sinuous portion to create a wave pattern upon rotation to macerate thrombus within the cerebral artery.

16. The neurovascular thrombectomy wire of claim 15, wherein the cable has a first diameter and the hypotube has a second diameter greater than the first diameter.

17. The neurovascular thrombectomy wire of claim 15, wherein the sinuous portion is movable from a straighter delivery position to a second position to expose the sinuous portion within the cerebral artery.

18. The neurovascular thrombectomy wire of claim 17, further comprising a coil at a distal tip portion of the wire.

* * * * *